United States Patent [19]

Shabel

[11] Patent Number: 4,530,235
[45] Date of Patent: Jul. 23, 1985

[54] RAPID DETERMINATION OF METAL STRENGTH FROM HARDNESS TESTS

[75] Inventor: Barrie S. Shabel, Murrysville, Pa.
[73] Assignee: Aluminum Company of America, Pittsburgh, Pa.
[21] Appl. No.: 544,735
[22] Filed: Oct. 24, 1983
[51] Int. Cl.³ .............................................. G01N 3/42
[52] U.S. Cl. ...................................................... 73/81
[58] Field of Search ................................ 73/81, 83, 85

[56] References Cited

U.S. PATENT DOCUMENTS 3,969,928 7/1976 Zarka ..................................... 73/81
4,331,026 5/1982 Howard .................................. 73/81

Primary Examiner—S. Clement Swisher
Attorney, Agent, or Firm—Elroy Strickland

[57] ABSTRACT

Means and method for making rapid determinations of the strength of metal materials from hardness evaluations of the materials. The means comprises at least two indentors for making impressions in a metal material, the indentors having predetermined dimensions. Apparatus for mechanically directing the indentors against the material are provided and mechanically connected to the indentors. The driving apparatus translates the indentors against the material under predetermined loads and in a manner that makes impressions in the material, the geometric configurations of which correspond to the configurations of the indentors. Means are provided for characterizing the respective geometries of the impressions, and means are provided for utilizing the dimensions of the indentors, the values of the applied loads, and the respective geometries, for calculating the yield and/or tensile strength of the material therefrom.

4 Claims, 2 Drawing Figures

RAPID DETERMINATION OF METAL STRENGTH FROM HARDNESS TESTS

BACKGROUND OF THE INVENTION

The invention relates generally to apparatus and procedures for making rapid determination of the strength of metal materials from hardness evaluation of the materials, and particularly to the elimination of errors and uncertainties in conventional hardness testing techniques that relate yield and/or tensile strength to hardness.

Hardness tests are commonly employed in quality assurance testing to indicate material strength. Typically, correlations for particular alloy-temper combinations are expressed as equations relating strength (S) to an observed hardness member (H) in the form of $$S = a + b \times H \qquad (1)$$

where the values of a and b depend on the hardness test scale selected.

Small scale tests, such as hardness tests, are convenient and less expensive than tests involving machined or otherwise especially prepared specimens for tensile testing. However, such convenience has led to a bewildering variety of hardness test scales. Generically, these can be divided into scales using ball-shaped indentors such as the Brinell and Rockwell indentors or diamond-shaped indentors such as Vickers or Knoop.

One significant disadvantage of the Rockwell test lies in the large variety of scales, i.e., no single scale adequately spans the whole range of interest for aluminum alloys, for example. Each scale has an optimal application in terms of material strength (temper) and minimum thickness necessary to avoid the so-called anvil effect, which effect involves variations in hardness readings due to the hardness of the structure supporting the specimen.

Nonetheless, for approximate practical purpose, the Rockwell scales can be ranked in terms of their severity of loading by dividing the applied measured load (L) by the diameter of the ball squared ($D^2$), which is the ratio $L/D^2$. If the reading on a particular scale is above say 100 (a hardness number), one has to then provide a scale with lower numerical readings; if the normal scale produces low readings, such as values below 20, a scale with a lower $L/D^2$ value is needed. This often necessitates changing scales in the midst of an investigation, which further complicates the use of a strength hardness equation such as equation (1) above.

Rockwell and other hardness tests, in addition, do not provide unambiguous predictions of yield or tensile strength of materials tested. This is the result of the influence of work hardening that occurs in the process of making the impressions. This influence can be understood by expressing hardness as a flow stress and releating it to yield or tensile strength through the well-known, constitutive stress-strain relationship.

The general conclusion from such analyses has been that one must know the work-hardening coefficient and the degree of strain imparted by the indentation process to predict yield or tensile strength from a hardness number.

An empirical way of circumventing the need for such complete knowledge was proposed in an article entitled "Estimating Yield Strength from Hardness Data" by Robert A. George, Subimal Dinda and Arthur S. Kasper, published in the May 1976 issue of *Metal Progress*, the authors use the basic relationship between applied load (L), indentor diameter (D) and the impression (d) of the form $$L/d^2 = A (d/D)^m \qquad (2)$$

to predict yield strengths of various steels. (A and m are empirical constants.) This work correlated yield strength with the constant A in the form of a regression equation, i.e., $$ys \ (ksi) = 0.325A \qquad (3)$$

with A being determined from nomographs of A versus a particular Rockwell number.

BRIEF SUMMARY OF THE INVENTION

The present invention takes into account the work hardening phenomenon that occurs in hardness evaluations that use mechanical indentors, thereby providing more precise estimates of both the yield and tensile strength from the results of such hardness evaluations. The invention uses the basic relationship of equation (2), the quantity $L/d^2$ in the equation is equal to $(\pi/4)$ times the "Meyer" hardness and is analogous to the stress which a specimen experiences in tensile testing.

The invention further uses the known empirical observations that the effective strain ($\epsilon$) in the volume of metal being deformed by an indentor is related to the diametral ratio $$\epsilon_{eff} = \alpha(d/D) \qquad (4)$$

where $0.2 < \alpha < 0.4$. Since Meyer hardness is analogous to stress, there is a similarity between equation (2) and the familiar power law equation $$\alpha = k\epsilon^h \qquad (5)$$

that represents the true stress ($\alpha$) and strain ($\epsilon$) behavior of metal material in the range of uniform plastic elongation.

Using these considerations, the present invention employs the concept of rapidly testing materials with different L and D combination to determine A and m using the above equation (2). A low strain flow stress value of $L/d^2$, i.e., at $d/D$ less than 0.2 (typically at $d/D = 0.1$), is calculated and designated as A'. The values of A and A' are then correlated respectively with tensile and yield strength of the material tested, the use of two or more load and diameter combinations providing two or more points to obtain an accurate slope for a proper stress-strain curve for the material.

DESCRIPTION OF THE DRAWINGS

The advantages and objectives of the invention will be best understood from consideration of the following detailed description and the accompanying drawings, FIG. 1 of which is a diagrammatic representation of a system for making hardness tests and for calculating material strength therefrom, while FIG. 2 of the drawings is a flow diagram of the processes of the system.

PREFERRED EMBODIMENTS

Figure 1:
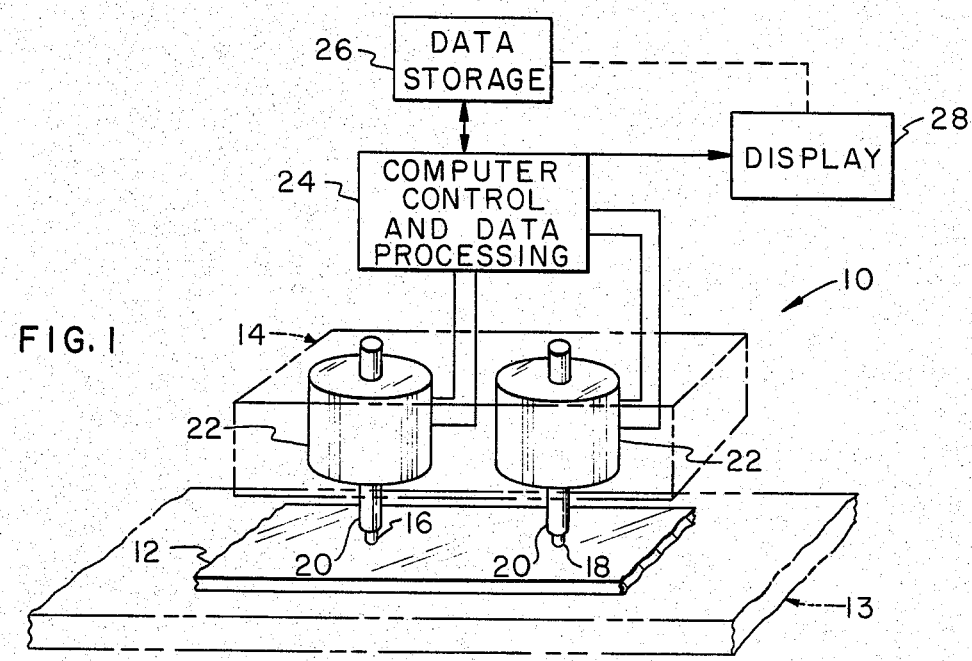

Referring now to the drawings, a system 10 is depicted schematically for rapidly providing two impressions (not shown) in a metal workpiece 12, and for controlling and measuring the impression. Workpiece 12 is shown supported on a structure 13 that is rigid for purpose of making hardness tests involving the workpiece.

System 10 includes means, generally designated 14, adapted to translate two indentors 16 and 18 against workpiece 12 to form the two impressions. Each indentor is shown supported at the end of a probe structure 20 extending from a respective actuator (cylinder) 22. The number of indentors shown in FIG. 1 is given by way of example only. The number of indentors or impressions employed in the system and their corresponding actuators in the basic process of the system of the invention need only be greater than one.

Similarly, the indentors shown in the drawing, and used in the experiments leading to the invention, are ball or spherical structures employed in Rockwell scale hardness evaluations. Rockwell scale evaluations were employed for their convenience only; the underlying methodology of the invention is not limited to any particular type of axisymmetric indentor and hardness measuring system.

In the drawing, indentor 16 is shown as the largest of the two, and indentor 18 is depicted as the smallest. The indentors, however, can be of the same size (diameter) if the loads at which the indentors are applied to workpiece 12 are different. Hence the indentor sizes shown in FIG. 1 represent two different load-diameter combinations.

The indentors can be applied to workpiece 12 by any suitable mechanism. One such mechanism is a double acting pneumatical cylinder (22), such as is shown in U.S. Pat. No. 4,331,026 to Howard et al. A single such cylinder can be employed to drive both indentors simultaneously if (again) the indentors are of different diameters, or, each indentor can be provided with its own cylinder, as shown in FIG. 1. Individual cylinders allow sequential operation of the indentors and the choice of loads (forces) at which the indentors are applied. These functions can be performed by a small computer 24 (a minicomputer or microprocessor) appropriately programmed and connected to the indentor actuators 22.

The indenting mechanisms are also provided with means (not shown) to measure the depths of the impressions made in workpiece 12. These can be, for example, commercially available, linear voltage differential transformers (LVDTs). Each LVDT has a stationary winding and an associated ferromagnetic core that moves with the probe of the indentor. The movement of the core changes the magnetic coupling between primary and secondary component of the stationary winding to provide an output voltage indicative of the displacement of the core and hence the depth of penetration by the indentor. The diameter of each impression can be calculated, for example, by computer 24, from the impression depth and the diameter of the indentor, which is known.

Other means, such as optical devices, using light sources and detectors, can be employed to characterize the size of the impressions made in workpiece 12.

The operation of arrangement 10 is as follows. The workpiece (12) to be rapidly tested for its strength, which workpiece may be a metal plate or sheet product, an extrusion or forging, wire rod or bar product, etc., is first placed on a rigid structure and surface 13 (which should conform to the shape of the product).

The diameters of the ball indentors and the loads under which the balls will be moved against the workpiece or product are chosen for the particular alloy and hardness of the product or workpiece. And, as discussed hereinafter, the system of the invention is suitable for establishing hardness to strength relationships for a variety of metal products, these relationships being employed for comparison to hardness readings obtained by the system when examining products for determination of their strengths.

With generally appropriate ball diameters and loads chosen for the particular material of the workpiece, the load values and ball diameter information are loaded in computer 24, and the device 14 ordered to drive the indentors 16 and 18 against the exposed face of the workpiece.

The means for indicating the depths of the impressions made by balls 16 and 18 in product 12, i.e., the above-described LVDTs for example, outputs depth signals to computer 24. The diameters of the impressions are then calculated using well-known geometric procedures since the diameters of the ball indentors are already known by the computer.

Figure 2:
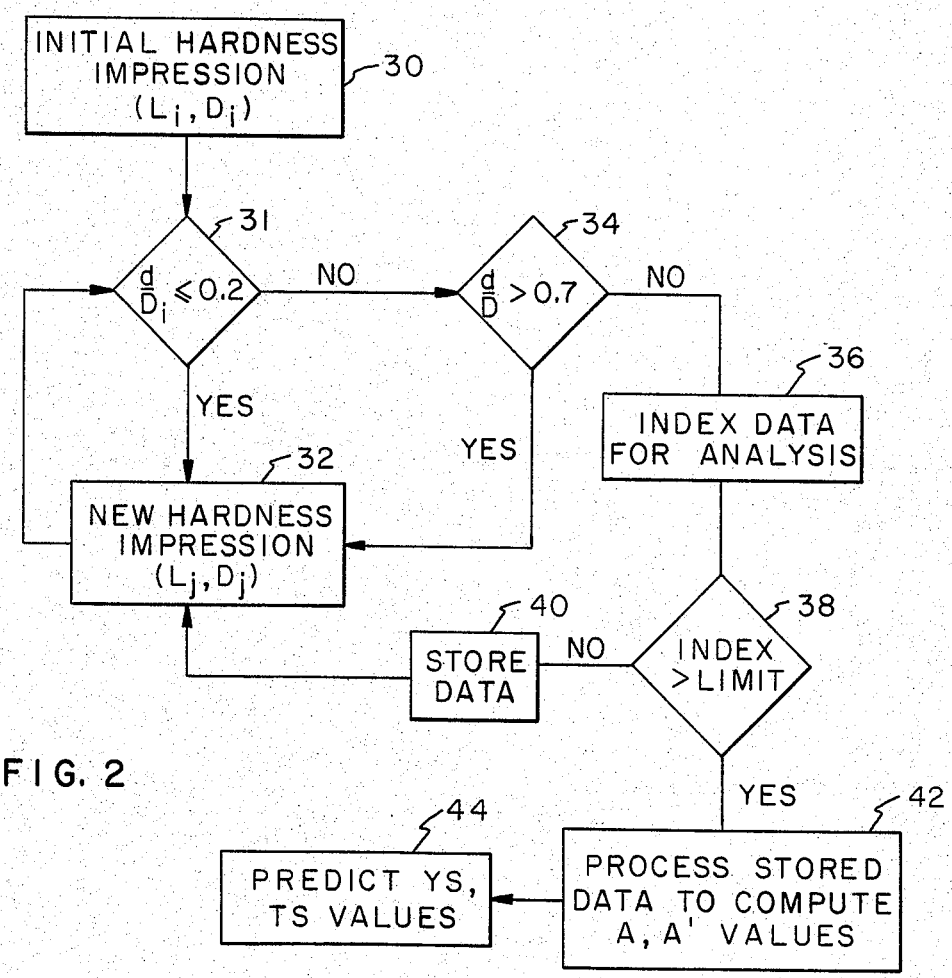

The process of the analysis of the invention as performed by computer 24 and a storage device 26 discussed in detail hereinafter is better explained by the flowchart of FIG. 2. More particularly, at location or box 30 in FIG. 2 a person operating the system 10 calls for an initial impression by one of the indentors 16 or 18. If the impression diameter ratio (d/D) is characterized at 31 as being less than 0.2, which is a "yes" answer for the logic of 31, the computer calls for another, deeper impression at 32 using a greater load (via cylinder 22) applied to the indentor or a smaller indentor with the same load. This step is repeated until an indentation of sufficient depth is made and a "no" answer is forthcoming from 31.

With the "no" answer from 31, the computer now tests at 34 whether the indentation or impression ratio d/D is greater than say 0.7. If the answer from 34 is "yes", another impression is again ordered at 32 using conditions that will result in d/D being less than 0.7 (but greater than 0.2). When this occurs, a "no" answer is produced at 34.

Available to computer 24 and to operating personnel via a display device 28 are now at least two distinct indications of the hardness of the product, i.e., at least two combinations of L and D at which the two indentors moved into the material of 12.

With a "no" answer from decision 34 the number of data points of impression characterizations, i.e., of load values to diameter ratios ($L/d^2$) denoting hardness of the workpiece is indexed at 36 for future analysis. However, if the number of points now available is not considered adequate (at 38) to provide good analysis and accurate prediction of the yield and tensile strength of the workpiece under test, the decision is made at 38 to store (at 40) the data of the points that have been made, and to order (again) additional impressions (at 32) until a sufficient number of hardness points are available.

With a sufficient number of data points, i.e., with a "yes" at 38, the computer processes at 42 certain data that is stored in 26 (FIG. 1) to provide predictions at 44 of the tensile and yield strength of the workpiece. This is accomplished in the following manner.

As indicated above, the parameter $L/d^2$ is analogous to the stress, and above equation (2) indicates a similarity to the well-known stress versus strain relationship involved in tensile testing of metal specimens [equation (5)] when strain is expressed mathematically by the above equation (4).

The similarity between above equation (2) and the power law representing the true stress to strain relationship in tensile analysis indicates that the work-hardening capability of the material under test can also be estimated from equation (2). This is typically done with standard linear regression techniques where m is simply the slope of the longarithmic regression relating the $L/d^2$ and $d/D$ values. As a consequence, the low strain value correlates with yield strength while the high value correlates with tensile strength. For practical purposes, in experiments employing the principles of the subject invention, as explained hereinafter, it appears that a lower limit on $d/D$ is about 0.2.

The selectable loads and/or indentors employed in the process and system of the present invention provide the different L and D combinations to determine the A and m values via equation (2). The "low strain" flow stress, e.g., at $d/D=0.1$, is calculated by the computer and is designated A'. The high strain value (A) is calculated using the equation and corresponds to the value of $L/d^2$ at $d/D$ equal to 1.

The results of these determinations are then compared to relationships that have been previously established between tensile strength and value A, and between yield strength and value A', via prior tests of the material involving hardness and tensile evaluations. The results of these prior tests are stored in memory connected to computer 24 and designated 26 in the drawing. Computer 24 can then compare the readout of 14 with the results in 26 to correlate the tensile and/or yield strength determined from its calculations involving the impression geometry with the data stored in 26 (involving the prior established relationship of strength and hardness). For this process the computer uses the formulations:

$$TS = K_1 A \text{ and } YS = K_2 A' \tag{6}$$

where A is equal to $L/d^2$ at the value $d/D$ being equal to one, and is, in that sense, the constant A of equation (2), and A' is a calculated parameter equal to a relatively low value of $L/d^2$, with $d/D$ being a number lower than 0.2, while $K_1$ and $K_2$ are empirical constants respectively for the tensile and yield strengths of the material being examined.

The work that has heretofore been done in the area of relating strength to hardness, as indicated earlier, employed a "nomograph", as discussed above, using Rockwell numbers. By using at least three such numbers, a straight line plot was drawn, using the log of $L/d^2$ versus the log of $d/D$, which intersected an A line representing the metal's A value or resistance to penetration. The A value, as determined by such a method, is at the high end of the scale, with $d/D$ being equal to 1.0 (one), and is a single value that is employed to estimate the yield strength of the metal tested and plotted from this initial hardness measure of the metal under test.

The system of the invention of course can be used to provide the data for storage in 26. By using the impression geometry provided by device 14 and at least two impressions in the material under test and fitting the same to equations (2) and (6), the strength to hardness relationship obtained thereby can be loaded into 26 for future correlation purposes.

The system of the present invention is employed as a control tool to conveniently monitor such processes as annealing, heat treating and artificial aging of metal products, as well as such mechanical processes as metal rolling and forming. This is particularly important in processes that directly affect the strength of the product produced.

While the invention has been described in terms of preferred embodiments, the claims appended hereto are intended to encompass all embodiments which fall within the spirit of the invention.

What is claimed is:

1. Apparatus for rapidly determining yield and/or tensile strength of a metal material from hardness evaluations thereof, comprising:
   at least two indentors for making at least two impressions in a metal material,
   means mechanically connected to the respective indentors for moving the same against the material,
   means for selecting a load level at which a first one of the indentors is moved against the material, and
   computer means for automatically selecting a larger level of load at which the second of the two indentors is applied against the material if the impression made by the first indentor is too shallow.

2. The apparatus of claim 1 in which the computer will select a smaller laod level for the second indentor if the impression made by the first indentor is too deep.

3. Apparatus for making rapid determinations of yield and/or tensile strength of metal materials from hardness evaluations of the materials, the apparatus comprising:
   at least two indentors having predetermined dimensions for making rounded impressions in a metal material,
   means mechanically connected to the indentors for directing the same against the material under respective, predetermined loads, and in a manner that makes impressions in the material of geometric configurations corresponding to the configurations of the indentors, and
   means for utilizing the loads applied to the respective indentors, the dimensions of the indentors, and the geometry of each impression, to calculate the yield and/or tensile strength therefrom,
   said means for utilizing the applied loads, indentor dimensions and impression geometry includes a computer capable of estimating A and m from hardness data using the equation $$L/d^2 = A (d/D)^m$$

where
   L is each of the applied loads,
   d is each of the diameters of the rounded impressions,
   D is each of the diameters of the indentors,
   A is a constant that indicates resistance of the material that limits penetration by a spherical indentor, and
   m is a measure of the working hardening characteristic of the material.

4. The apparatus of claim 3 in which the computer includes means for storing hardness data and means for relating the same to the tensile and yield strength of a particular material by utilization of the formulations $$TS = K_1 A$$

and $$YS = K_2 A'$$

where A is equal to $L/d^2$ at the value of d/D being equal to one, and

A' is a calculated parameter equal to $L/d^2$ at a relatively low value of d/D, such as a number less than 0.2, while $K_1$ and $K_2$ are empirical constants respectively for the tensile and yield strength of the particular material.

* * * * *